United States Patent
Fitzgerald et al.

(10) Patent No.: US 7,398,948 B2
(45) Date of Patent: Jul. 15, 2008

(54) RESPIRATORY DISEASE MANAGEMENT DEVICE AND RELATED METHOD

(75) Inventors: Craig Q. Fitzgerald, Raleigh, NC (US); Tyler S. Tibbits, Raleigh, NC (US)

(73) Assignee: Healthcarta, LLC, Raleigh, NC (US)

( * ) Notice: Subject to any disclaimer, the term of this patent is extended or adjusted under 35 U.S.C. 154(b) by 1366 days.

(21) Appl. No.: 10/263,478

(22) Filed: Oct. 3, 2002

(65) Prior Publication Data

US 2004/0065323 A1    Apr. 8, 2004

(51) Int. Cl.
A47K 1/08    (2006.01)
(52) U.S. Cl. .................. 248/205.2; 248/311.2; 248/318; 206/570; 206/459.5
(58) Field of Classification Search .............. 248/205.1, 248/205.2, 205.3, 206.5, 207, 309.1, 311.2, 248/313, 314, 318; 206/570, 438, 459.5, 206/828
See application file for complete search history.

(56) References Cited

U.S. PATENT DOCUMENTS

| | | | | |
|---|---|---|---|---|
| 5,613,660 A | * | 3/1997 | Wyatt | 248/300 |
| 6,053,340 A | * | 4/2000 | Cameron | 211/85.7 |
| 6,126,129 A | * | 10/2000 | Herron | 248/311.3 |
| 6,572,063 B1 | * | 6/2003 | Gitelman et al. | 248/314 |
| 2005/0017146 A1 | * | 1/2005 | Kringel et al. | 248/313 |
| 2005/0189258 A1 | * | 9/2005 | Vastola | 206/570 |

* cited by examiner

Primary Examiner—Jacob K. Ackun, Jr.
(74) Attorney, Agent, or Firm—Jenkins, Wilson, Taylor & Hunt, P.A.

(57) ABSTRACT

A device is provided for retaining a respiratory disease management device and for displaying respiratory disease management information. The device comprises a rear wall, first and second opposing side walls adjoining the rear wall, and a front wall extending from the first side wall. An attachment component secures the rear wall to an upright structural surface. The walls of the device define a partially enclosed retention space for holding a respiratory disease management device such as a respiratory disease medicine delivery device or a peak flow meter. A substrate such as a card is secured to the holding device, and displays printed matter comprising information relating to respiratory disease management.

25 Claims, 6 Drawing Sheets

RESPIRATORY DISEASE MANAGEMENT DEVICE AND RELATED METHOD

TECHNICAL FIELD

The present invention relates generally to the management of pulmonary diseases such as asthma and, more specifically, asthma management devices such as dosage delivery devices and peak flow meters, holding devices therefor, and accompanying informational displays.

BACKGROUND ART

In the treatment of respiratory diseases such as asthma and allergies, the distribution of asthma or allergy management devices such as therapeutic dosage delivery devices and respiratory assessment devices is for self-use by a patient according to a management strategy prescribed by the patient's health care provider. As is well known to persons skilled in the art, dosage delivery devices typically include a cartridge or housing that contains an asthma medicament in liquid or powder form, and an outlet adapted for delivering dosages to the patient orally or nasally. The medicament is either pre-loaded in the cartridge, or a package containing the medicament is loaded in the cartridge by the patient. The whole of such delivery devices can be disposable after one or more uses, or the cartridge can be reusable indefinitely with the package containing the medicine replaced when depleted. Depending on the severity of the pulmonary disease, a number of different kinds of medicines may be prescribed to a patient. For example, some medicines are indicated for prevention and must be administered on a repeated, regular basis, while other medicines are indicated for emergencies and administered only on an as-needed basis.

When the medicament is a liquid, it can be provided in the cartridge in bulk quantity, which requires the patient to administer the proper dosage through an inhalation means such as a nozzle. One common type of delivery device, often termed a metered dose inhaler, consists of a housing having an internal passage and an orifice. A canister equipped with a valve and containing pressurized liquid medicament is inserted by the patient into the housing, such that the stem of the valve is seated in the internal passage of the housing. To administer a dosage of the medicine, the patient actuates the device by pushing the canister and the housing towards each other, thereby opening the valve and releasing a properly metered dosage from the orifice. Alternatively, when the medicament is a powder, it can be distributed in a package containing pre-metered doses in individual packets (e.g., blisters), in which case the delivery device includes a patient-actuated means for puncturing each packet to deliver the dosage to the patient.

One example of a respiratory assessment device is the peak flow meter. When properly used, the peak flow meter enables the patient to track the severity of his or her asthma or related pulmonary condition over time and evaluate the effectiveness of his or her prescribed management strategy. Such a self-assessment provides useful feedback for the patient's health care provider, and can indicate whether the management strategy should be modified such as by changing the dosage schedule or selecting a different medicine.

In view of the foregoing, and as well known to persons skilled in the art, the success of any given asthma management strategy depends significantly on the efforts, knowledge, and skill of the patient. For instance, the patient must make proper use of the asthma management products according to the instructions provided, whether those products include dosage delivery devices or testing devices. It has been found, for example, that the improper actuation of inhaler products can result in the delivery of therapeutically ineffective dosages of medicine to the patient's respiratory system. In the case of testing devices, improper use can produce inaccurate data. In addition, the patient must adhere to the prescribed management strategy, including administering the correct medicine according to conditions and administering the correct dosage or number or dosages per day and at the correct times. Common reasons for the failure of a patient's management strategy include the absence of means for reminding the patient to use the prescribed management devices, and the lack of readily available information to keep the patient informed about his or her disease and about the proper use of the prescribed management devices.

It would therefore be advantageous to provide a device for holding and storing respiratory disease management devices in a highly visible location so as to remind a patient suffering from chronic respiratory diseases to adhere to his or her treatment schedule. It would be further advantageous to provide such a holding device with a display of information useful to the patient in the management of his or her disease. The present invention is provided to address these and other problems attending the management of respiratory-related disease.

DISCLOSURE OF THE INVENTION

The present invention provides a device for holding an respiratory disease management device, such as a medicament delivery device or a peak flow meter. The device is adapted for mounting in a conspicuous location such as the mirror or other upright structure of a user's bathroom or other room. The device includes a medium such as a card or other substrate on which printed matter is displayed. The printed matter comprises information useful to the user in regard to the successful management of the user's respiratory disease. The present invention further provides a method for assisting such user in the management of his or her disease.

According to one embodiment of the invention, a device is provided for removably retaining a respiratory disease management device and for displaying respiratory disease management information. The device comprises a rear wall, a first side wall, a second side wall, and a front wall. The rear wall comprises a rear wall inside surface and an opposing rear wall outside surface. The first side wall extends outwardly from the rear wall and comprises a first side wall inside surface. The second side wall extends outwardly from the rear wall and comprises a second side wall inside surface generally facing the first side wall inside surface. The front wall extends from the first side wall and comprises a front wall inside surface generally facing the rear wall inside surface. The rear wall, front wall, and first and second side walls define a partially enclosed retention space. The retention space is adapted for removably retaining a respiratory disease management device therein. The first and second side wall inside surfaces are shaped to substantially conform to an outer profile of the respiratory disease management device. An attachment component is secured to the rear wall for attaching the rear wall outside surface to a structural surface, such as a mirror or wall of the user's bathroom.

A substrate is secured to the rear wall, and displays printed matter comprising information relating to respiratory disease management. The printed matter can comprise respiratory disease care provider contact information, respiratory disease-related product source information, respiratory disease-related educational information, and/or respiratory disease medicine treatment information.

According to another embodiment of the present invention, an respiratory disease management system comprises a holding device, an attachment component, a substrate, and an respiratory disease management device. The holding device comprises a rear wall, first and second opposing side walls adjoining the rear wall, and a front wall extending from the first side wall. The rear wall, front wall, and first and second side walls define a partially enclosed retention space. The attachment component is secured to the rear wall and is adapted for attaching the rear wall to a structural surface. The substrate is secured to the holding device and displays printed matter comprising information relating to respiratory disease management. The respiratory disease management device is removably disposed in the retention space in contact with the holding device. The respiratory disease management device is a respiratory disease medicine delivery device or a peak flow meter device.

According to yet another embodiment of the present invention, a respiratory disease management kit comprises a package suitable for mail shipment, and which contains a holding device, an attachment component, a substrate, and a respiratory disease management device as described herein.

The present invention also provides a method for assisting a respiratory disease patient in managing a respiratory disease-related disease afflicting the patient. The method comprises providing a holding device and a substrate adapted for securement to the holding device. The holding device comprises a rear wall, first and second opposing side walls adjoining the rear wall, a front wall extending from the first side wall, and an attachment component for securing the rear wall to an upright structural surface. The rear wall, front wall, and first and second side walls define a partially enclosed retention space adapted for removably retaining a respiratory disease management device therein. The substrate displays printed matter comprising information relating to respiratory disease management.

It is therefore on object of the present invention to provide a device for removably retaining a respiratory disease management product such as a dosage delivery device or peak flow meter when such respiratory disease management product is not in use.

It is another object of the present invention to provide such a retaining device that is adapted for mounting at a conspicuous location to promote and facilitate proper use of the respiratory disease management product in accordance with a respiratory disease management strategy indicated for a given patient.

It is yet another object of the present invention to provide information displayable by such retaining device to assist a patient in carrying out his or her respiratory disease management strategy.

Some of the objects of the invention having been stated hereinabove, and which are addressed in whole or in part by the present invention, other objects will become evident as the description proceeds when taken in connection with the accompanying drawings as best described hereinbelow.

DETAILED DESCRIPTION OF THE INVENTION

As used herein, the term "respiratory disease" is broadly meant to encompass any disease or affliction affecting the upper or lower respiratory system. Non-limiting examples include asthma, allergies, allergic rhinitis, and chronic obstructive pulmonary disease (COPD) such as chronic bronchitis and emphysema.

Figure 1A:
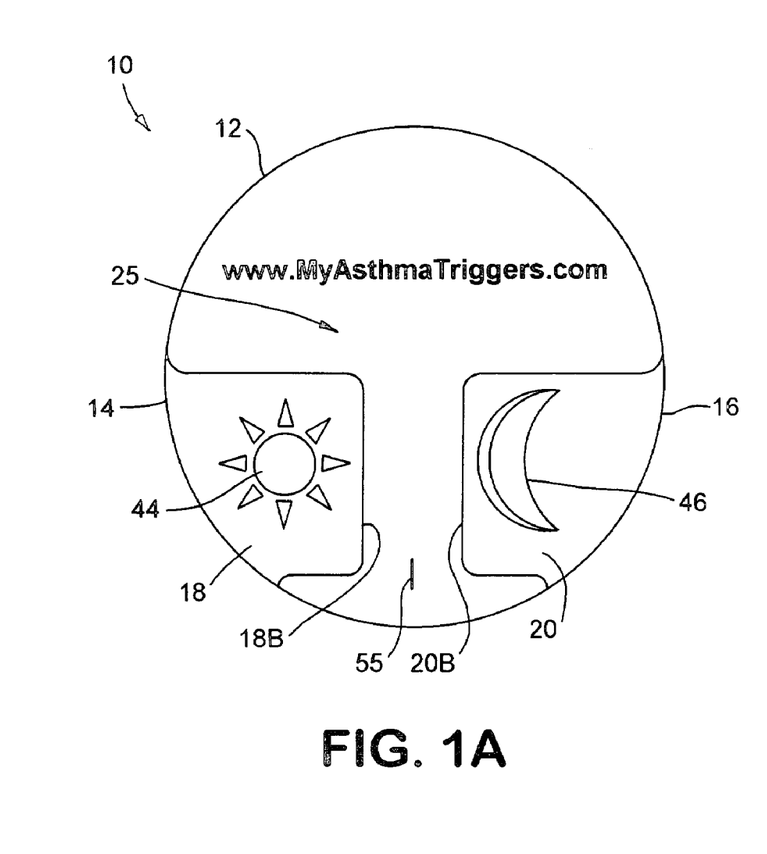
FIG. 1A is a front elevation view of a respiratory disease management product holding device provided according to one embodiment of the present invention.
Figure 1B:
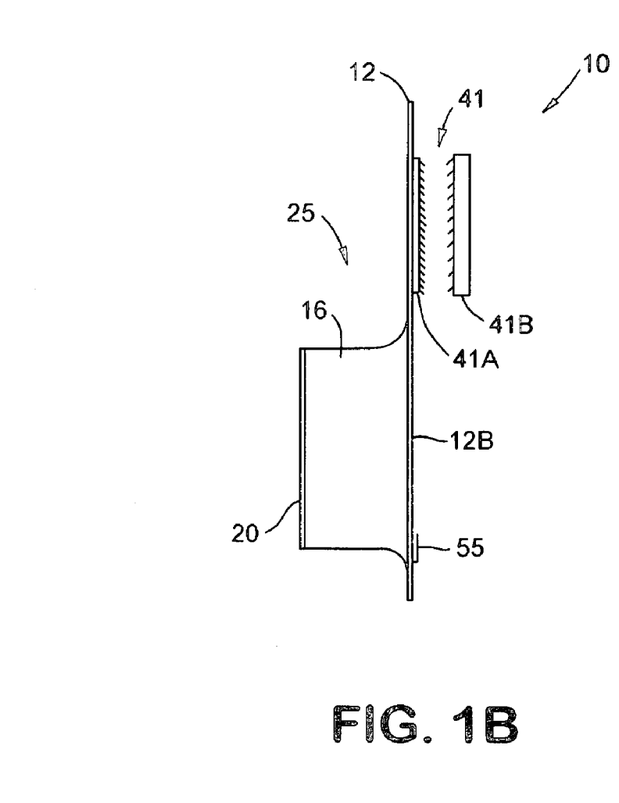
FIG. 1B is a side elevation view of the holding device illustrated in FIG. 1A.
Figure 1C:
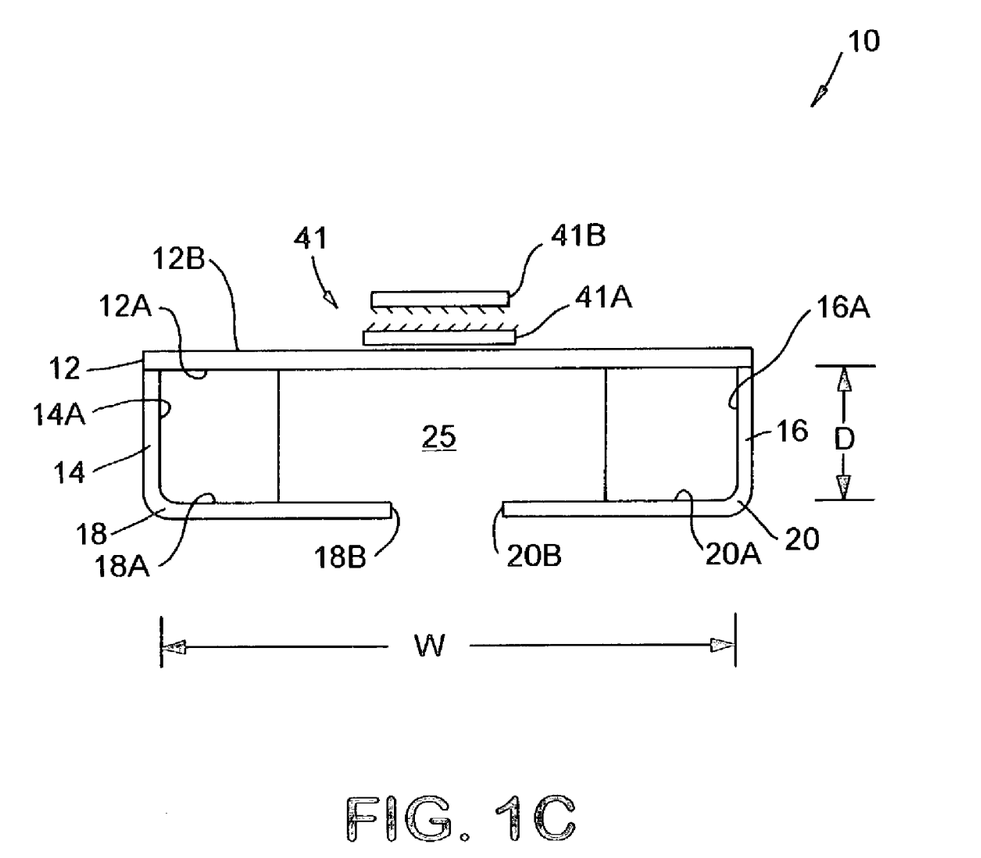
FIG. 1C is a top plan view of the holding device illustrated in FIG. 1A.

Referring now to FIGS. 1A-1C, a holding device, generally designated 10, is illustrated in accordance with a preferred embodiment of the invention. Preferably, holding device 10 is constructed as a unitary body from a molded polymeric material such as polyethylene, LEXAN® material, or the like. Preferably, the polymeric material is clear (e.g., translucent or transparent) so as not to obstruct a user's view of a respiratory disease-related management device retained by holding device 10. The body of holding device 10 comprises a rear wall 12 and one or more side walls, such as first and second side walls 14 and 16, extending outwardly at an angle from rear wall 12 at or near its perimeter. A front wall is provided and preferably comprises one or more front wall portions 18 and 20, such as first and second front wall portions 18 and 20 illustrated in FIGS. 1A-1C. First front wall portion 18 extends at an angle from first side wall 14, and second front wall portion 20 extends at an angle from second side wall 16. By this configuration, rear wall 12, first and second side walls 14 and 16, and first and second front wall portions 18 and 20 define a partially enclosed retention space or basket, generally designated 25. As shown in FIG. 1C, retention space 25 has a depth D bounded between an inside surface 12A of rear wall 12 and respective inside surfaces 18A and 20A of first and second front wall portions 18 and 20, and a width W bounded between respective inside surfaces 14A and 16A of first and second side walls 14 and 16.

The shape (e.g., disk-shaped, box-shaped, or the like) and the dimensions of retention space 25 will depend on the specific respiratory disease management device to be retained therein. Accordingly, depth D and/or width W can vary as appropriate for defining the desired shape of retention space 25. In the example illustrated in FIGS. 1A-1C, depth D is approximately 1 1/16 inches and width W varies along respective inside surfaces 14A and 16A of first and second side walls 14 and 16 to a maximum value of approximately 3 7/16 inches. In the second embodiment of the invention illustrated in FIGS. 3A and 3B, depth D is approximately 15/16 inch and width W varies along respective inside surfaces 14A and 16A of first and second side walls 14 and 16 to a maximum value of approximately 2⅝ inches.

Figure 2A:
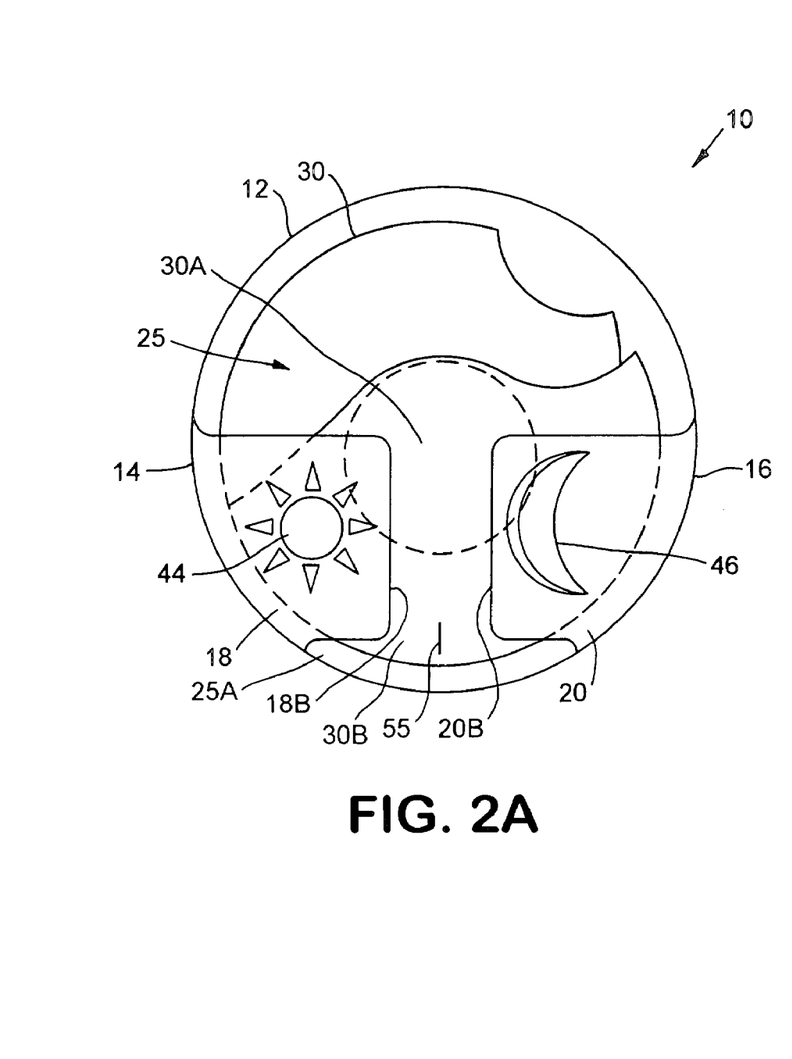
FIG. 2A is a front elevation view of the holding device illustrated in FIG. 1A, showing a respiratory disease management product retained therein.
Figure 2B:
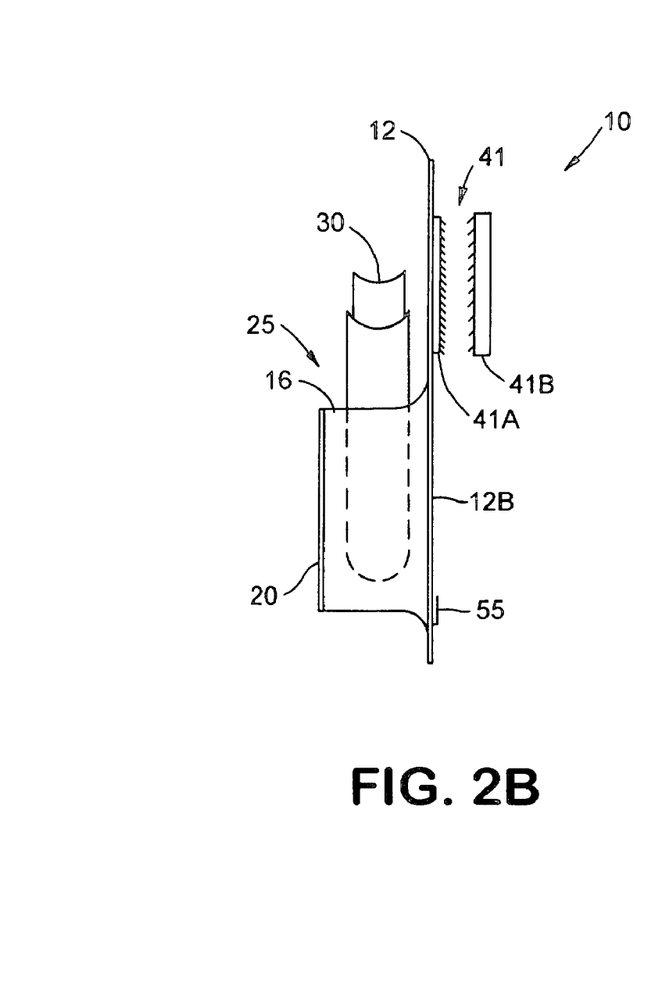
FIG. 2B is a side elevation view of the holding device with the respiratory disease management product retained therein.

Referring now to FIGS. 2A and 2B, holding device 10 is designed to permit a respiratory disease patient to easily load a respiratory disease management device into retention space 25 for storage, and remove such respiratory disease management device from retention space 25 when usage of the respiratory disease management device is indicated in accordance with a respiratory disease management program specific to the patient. As one example of a respiratory disease management device, illustrated in FIGS. 2A and 2B, an asthma medicine delivery device 30 is retained by holding device 10. To facilitate loading and removal of asthma medicine delivery device 30, first and second front wall portions 18 and 20 terminate at respective first and second front wall lateral edges 18B and 20B that face each other and are separated by a gap, such that a central portion 30A of asthma medicine delivery device 30 remains exposed. In addition, a lowermost section 25A of retention space 25 is open, such that a lower portion 30B of asthma medicine delivery device 30 remains exposed. These features afford the respiratory disease patient a significant amount of freedom in manipulating asthma medicine delivery device 30 during loading and unloading thereof into and out from holding device 10.

As indicated above, the structural features of holding device 10 that define retention space 25 can be contoured as necessary to substantially conform to the outer profile of asthma medicine delivery device 30 and thereby improve the fit between asthma medicine delivery device 30 and holding device 10. For example, in the embodiment illustrated in FIGS. 1A-2B, asthma medicine delivery device 30 is a disk-shaped device for delivering metered doses of asthma medicine in powder form. An example of such a disk-shaped device is commercially available from Glaxo Group Limited, Middlesex, United Kingdom, for the delivery of ADVAIR® medicine. Inside surfaces 14A and 16A of first and second side walls 14 and 16 of holding device 10 are rounded so as to conform to this disk shape. It will be understood, however, that other structural features of holding device 10, such as one or more of the surfaces or edges of rear wall 12 or first and second front wall portions 18 and 20, could also be contoured in accordance with the invention as necessary to conform to the outer shape of the particular asthma medicine delivery device 30 or other respiratory disease management device to be retained by holding device 10. It will also be understood that the invention is not limited to use in connection with disk-shaped asthma medicine delivery devices 30. A wide variety of types and shapes of commercially available respiratory disease medicine delivery devices are well-known to persons skilled in the art. Another example is an oral inhalation device consisting of a canister of pressurized asthma medicine in liquid form connected to an L-shaped housing used for actuating an internal valve of the canister to deliver metered aerosolized doses to the patient. An additional example is a nasal inhalation device consisting of a bottle containing non-pressurized medicine in liquid form that is attached to an upright applicator.

Figure 3A:
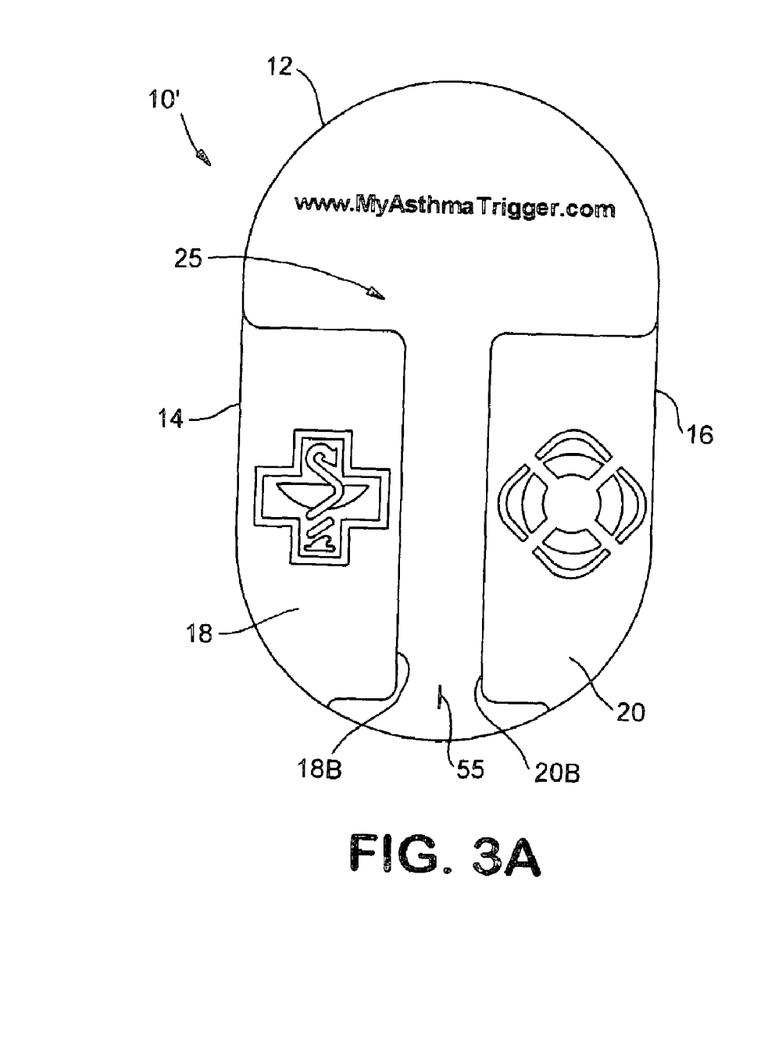
FIG. 3A is a front elevation view of a respiratory disease management product holding device provided according to another embodiment of the present invention.
Figure 3B:
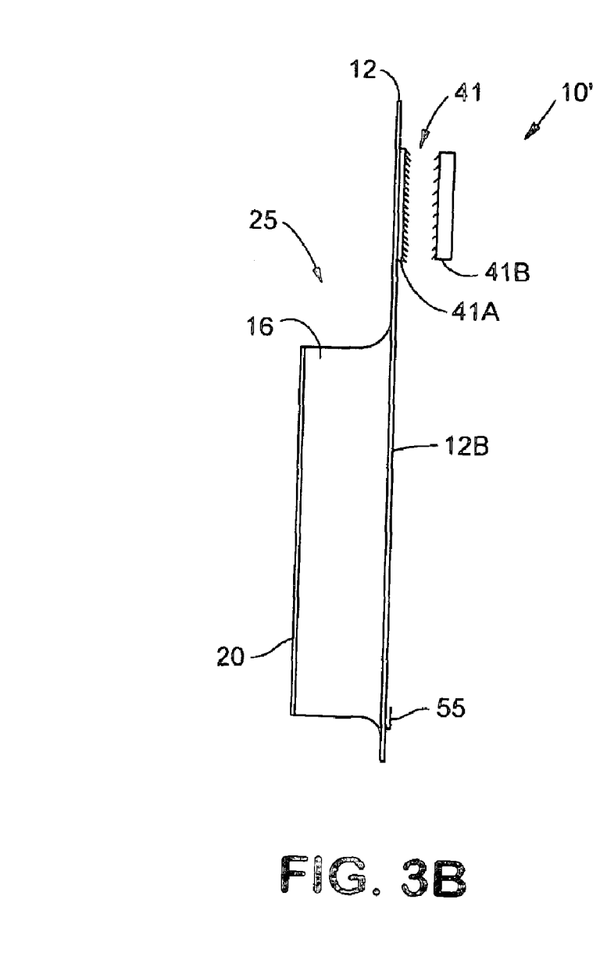
FIG. 3B is a side elevation view of the holding device illustrated in FIG. 3A.
Figure 4A:
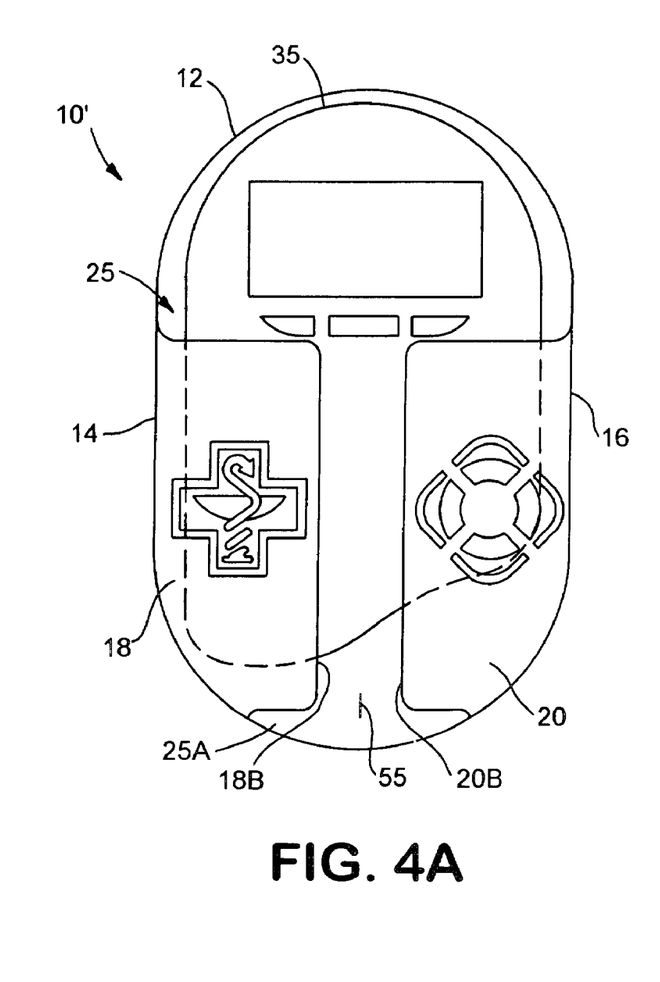
FIG. 4A is a front elevation view of the holding device illustrated in FIG. 3A, showing a respiratory disease management product retained therein.
Figure 4B:
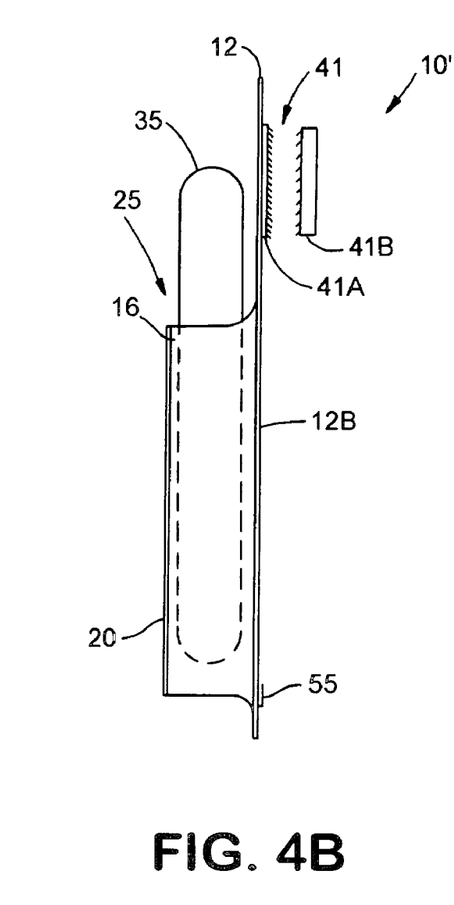
FIG. 4B is a side elevation view of the holding device illustrated in FIG. 4A.

In addition to asthma medicine delivery device 30, the invention contemplates the use of holding device 10 in connection with other types of respiratory disease management devices. Thus, FIGS. 3A and 3B illustrate a holding device, generally designated 10, configured as shown in FIGS. 3A and 3B can be used to retain a peak flow meter 35 as illustrated in FIGS. 4A and 4B. As known to persons skilled in the art, peak flow meters are used by respiratory disease patients to assess respiratory performance. It will be noted that throughout the present disclosure, all descriptions relating to holding device 10 likewise apply to holding device 10'.

In addition to retaining a respiratory disease management device (e.g., asthma medicine delivery device 30 of FIGS. 2A and 2B or peak flow meter 35 of FIGS. 4A and 4B) for storage between uses, a primary function and advantage of holding device 10 of the invention is to assist a respiratory disease patient in better managing his or her disease. To this end, holding device 10 is designed for use in a high-visibility environment that reminds the respiratory disease patient to use the respiratory disease management device, and thus promotes adherence by the respiratory disease patient to a proper strategy of usage of the respiratory disease management device, as determined by the treatment protocol specifically indicated for that patient. For instance, it is common for a respiratory disease patient to be instructed by a health care provider to administer doses of respiratory disease medicine in the morning and in the evening on a daily basis.

Hence, referring to FIGS. 1B, 1C, 2B, 3B and 4B, a mounting component, generally designated 41, is provided with holding device 10 for mounting holding device 10 in an upright, conspicuous fashion in an environment typically encountered by the patient during normal morning and evening activities, such the mirror, cabinet or wall of the patient's bathroom. In the exemplary embodiments illustrated herein, mounting component 41 comprises a hook and loop fastener system, such as a VELCRO® system, in which one portion 41A is adhered by conventional means to an outside surface 12B of rear wall 12 of holding device 10 and another removably interlocking portion 41B is adhered by conventional means to a conspicuous upright structure such as a mirror, cabinet, or wall. Additionally, informational content such as a day symbol 44 and a night symbol 46 can be molded or attached to a conspicuous portion of holding device 10, such as first and second front wall portions 18 and 20, to remind the patient that the respiratory disease management device retained by holding device 10 should be used in the course of regular morning and evening activities.

Figure 5:
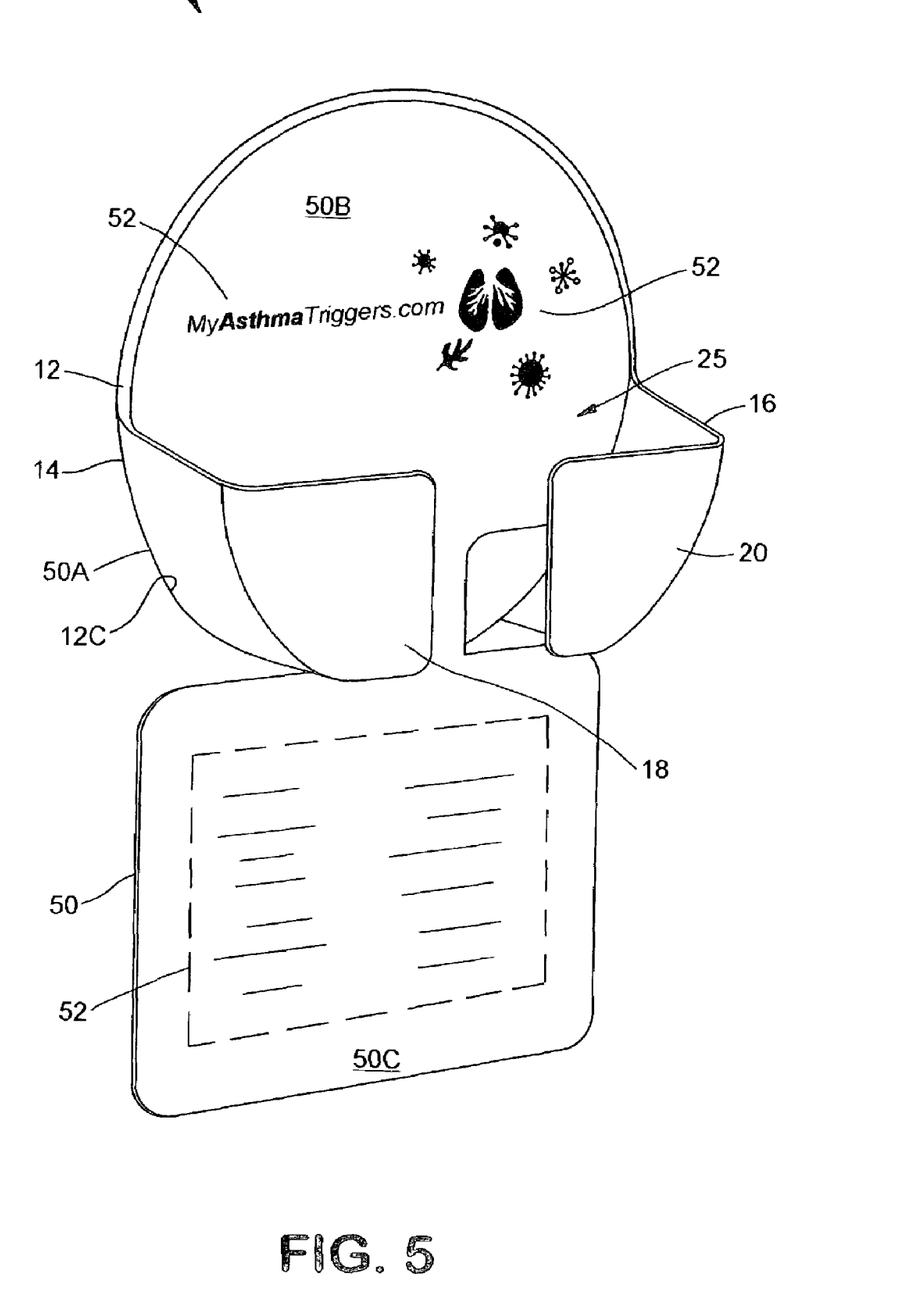
FIG. 5 is a perspective view of a holding device similar to that illustrated in FIG. 1A, with a substrate attached thereto on which printed matter relating to respiratory disease management is printed in accordance with the present invention.

Referring now to FIG. 5, according to another aspect of the invention, holding device 10 assists a respiratory disease patient in respiratory disease management by providing a substrate 50 such as a card that contains printed matter 52 in the form of text, photographs, images and/or other graphics comprising information useful to the respiratory disease patient. Such information can be generalized and/or specific to the individual user of holding device 10, and can contain, for example, respiratory disease care provider contact information such as telephone numbers and internet addresses; respiratory disease-related product source information such as prescription ordering information, brand designations, and trademark information; respiratory disease-related educational information such as local environmental conditions known to trigger respiratory disease-related complications; and/or respiratory disease medicine treatment information such as prescribed dosages and dosage schedule. It can thus be seen that holding device 10 with substrate 50 is also useful for marketing and promoting products and services relating to respiratory disease management.

Substrate 50 is attached holding device 10 so as to be readily displayable to and easily viewable by the user. Thus, in the example illustrated in FIG. 5, substrate 50 is attached to rear wall 12 such that the information printed on substrate 50 faces the user. While an adhesive backing could be provided with substrate 50 for adhering substrate 50 to rear wall 12 or another portion of holding device 10, the means employed for securing substrate 50 to holding device 10 preferably permits substrate 50 to be easily removed and replaced with another substrate for purposes of providing new or updated information. Thus, to removably attach substrate 50 against rear wall 12, one or more slots 12C are formed at the interface of rear wall 12 and first and/or second side walls 14 and 16 and a tabbed portion 50A of substrate 50 is inserted into each slot. Alternatively, as shown in FIGS. 1A, 1B, 2A, 2B, 3A, 3B, 4A and 4B, one or more tabs or hooks 55 can be formed or attached to either side of rear wall 12 to retain substrate 50 against, or hang substrate 50 from, rear wall 12. Referring back to FIG. 5, substrate 50 can comprise an upper section 50B abutting rear wall 12 in retention space 25, and a lower section 50C hanging from rear wall 12 or otherwise disposed below retention space 25. Alternatively, substrate 50 can solely comprise either upper portion 50B or lower portion 50C.

From the foregoing, it is seen that the ability to easily replace substrate 50 with another substrate facilitates tailoring the use of holding device 10 to the specific needs of individual respiratory disease patients. Moreover, this ability facilitates coordination between the supplier or reseller of holding device 10 and the supplier or reseller of the accompanying respiratory disease management device or the provider of respiratory disease care services.

It will be understood that the term "asthma" as used herein in various forms relates not only to asthma-specific disease and management but also respiratory-related diseases and management.

It will be further understood that various details of the invention may be changed without departing from the scope of the invention. Furthermore, the foregoing description is for the purpose of illustration only, and not for the purpose of limitation, as the invention is defined by the claims as set forth hereinafter.

What is claimed is:

1. A device for removably retaining a respiratory disease management device and for displaying respiratory disease management information, comprising:
   (a) a rear wall comprising a rear wall inside surface and an opposing rear wall outside surface;
   (b) a first side wall extending outwardly from the rear wall and comprising a first side wall inside surface;
   (c) a second side wall extending outwardly from the rear wall and comprising a second side wall inside surface generally facing the first side wall inside surface;
   (d) a front wall extending from at least one of the first and second side walls and comprising a front wall inside surface generally facing the rear wall inside surface, wherein the rear wall, front wall, and first and second side walls define a partially enclosed retention space adapted for removably retaining a respiratory disease management device therein, and wherein the first and second side wall inside surfaces are shaped to substantially conform to an outer profile of the respiratory disease management device;
   (e) an attachment element secured to the rear wall for attaching the rear wall outside surface to a structural surface; and
   (f) a substrate secured to the rear wall and displaying printed matter comprising information relating to respiratory disease management.

2. The device according to claim 1 wherein the rear wall, front wall, and first and second side walls are composed of a substantially clear polymeric material.

3. The device according to claim 1 wherein the front wall extends inwardly from the first and second side walls and defines an open space therein.

4. The device according to claim 1 wherein the front wall comprises first and second front wall portions, the first front wall portion extends from the first side wall and comprises a first front wall lateral edge, the second front wall portion extends from the second side wall and comprises a second front wall lateral edge facing the first front wall lateral edge, and the first and second front wall lateral edges define a gap therebetween adapted for facilitating access by a respiratory disease management participant to a respiratory disease management device disposed in the retention space.

5. The device according to claim 1 wherein the attachment element comprises a hook and loop fastener system comprising a first portion attached to the rear wall outside surface and a second portion interlockable with the first portion and adapted for adherence to the structural surface.

6. The device according to claim 1 comprising a tab affixing the substrate to the rear wall.

7. The device according to claim 6 wherein the tab is disposed on the rear wall outside surface.

8. The device according to claim 6 wherein the tab is disposed on the rear wall inside surface.

9. The device according to claim 1 wherein the substrate is adhered to the rear wall.

10. The device according to claim 1 wherein the substrate comprises an upper portion adjacent to the rear wall and a lower portion disposed below the retention space.

11. The device according to claim 1 wherein the printed matter displayed on the substrate comprises information selected from the group consisting of respiratory disease care provider contact information, respiratory disease-related product source information, respiratory disease-related educational information, respiratory disease medicine treatment information, and combinations thereof.

12. A respiratory disease management system comprising:
   (a) a holding device comprising a rear wall, first and second opposing side walls adjoining the rear wall, and a front wall extending from at least one of the first and second side walls, wherein the rear wall, front wall, and first and second side walls define a partially enclosed retention space;
   (b) an attachment element secured to the rear wall for attaching the rear wall to a structural surface;
   (c) a substrate secured to the holding device and displaying printed matter comprising information relating to respiratory disease management; and
   (d) a respiratory disease management device removably disposed in the retention space in contact with the holding device.

13. The system according to claim 12 wherein the front wall extends inwardly from the first and second side walls and defines an open space therein.

14. The system according to claim 12 wherein the front wall comprises first and second front wall portions, the first front wall portion extends from the first side wall and comprises a first front wall lateral edge, the second front wall portion extends from the second side wall and comprises a second front wall lateral edge facing the first front wall lateral edge, and the first and second front wall lateral edges define a gap therebetween adapted for facilitating access by a respiratory disease management participant to the respiratory disease management device retained in the retention space.

15. The system according to claim 12 wherein the first side wall comprises a first side wall inside surface, the second side wall comprises a second side wall inside surface, and the first and second side wall inside surfaces are shaped to substantially conform to an outer profile of the respiratory disease management device.

16. The system according to claim 12 wherein the printed matter displayed on the substrate comprises information selected from the group consisting of respiratory disease care provider contact information, respiratory disease-related product source information, respiratory disease-related educational information, respiratory disease medicine treatment information, and combinations thereof.

17. The system according to claim 12 wherein the respiratory disease management device comprises a respiratory disease medicine delivery device.

18. The system according to claim 12 wherein the respiratory disease management device comprises a peak flow meter device.

19. A respiratory disease management kit comprising:
- (a) a holding device comprising a rear wall, first and second opposing side walls adjoining the rear wall, and a front wall extending from at least one of the first and second side walls, wherein the rear wall, front wall, and first and second side walls define a partially enclosed retention space;
- (b) an attachment element adapted for securing to the rear wall and for attaching the rear wall to a structural surface;
- (c) a substrate adapted for securing to the holding device, the substrate displaying printed matter comprising information relating to respiratory disease management;
- (d) a respiratory disease management device adapted for being removably disposed in the retention space in contact with the holding device; and
- (e) a package containing the holding device, the attachment element, the substrate, and the respiratory disease management device and suitable for mail shipment.

20. The kit according to claim 19 wherein the printed matter displayed on the substrate comprises information selected from the group consisting of respiratory disease care provider contact information, respiratory disease-related product source information, respiratory disease-related educational information, respiratory disease medicine treatment information, and combinations thereof.

21. The kit according to claim 19 wherein the respiratory disease management device comprises an respiratory disease medicine delivery device.

22. The kit according to claim 19 wherein the respiratory disease management device comprises a peak flow meter device.

23. A method for assisting a patient in managing a respiratory disease afflicting the patient, comprising:
- (a) providing a holding device comprising a rear wall, first and second opposing side walls adjoining the rear wall, a front wall extending from at least one of the first and second side walls, and an attachment element for securing the rear wall to an upright structural surface, wherein the rear wall, front wall, and first and second side walls define a partially enclosed retention space adapted for removably retaining an respiratory disease management device therein;
- (b) providing a substrate adapted for securement to the holding device and displaying printed matter comprising information relating to respiratory disease management; and
- (c) managing a respiratory disease related disease by using the respiratory disease management device with reference to the printed matter on the substrate.

24. The method according to claim 23 wherein the retention space is adapted for retaining a respiratory disease medicine delivery device and the printed matter displayed on the substrate comprises information relating to the use of the respiratory disease medicine delivery device.

25. The method according to claim 23 wherein the retention space is adapted for retaining a peak flow meter device and the printed matter displayed on the substrate comprises information relating to the use of the peak flow meter device.

* * * * *